United States Patent
Monsalve et al.

(10) Patent No.: US 10,092,891 B2
(45) Date of Patent: Oct. 9, 2018

(54) CONTROLLING THE ACTIVITY OF GROWTH FACTORS, PARTICULARLY TGF-β, IN VIVO

(71) Applicant: University of Florida Research Foundation, Incorporated, Gainesville, FL (US)

(72) Inventors: Adam Monsalve, Gainesville, FL (US); Jon P. Dobson, Gainesville, FL (US)

(73) Assignee: University of Florida Research Foundation, Incorporated, Gainesville ( * ) Notice: Subject to any disclaimer, the term of this patent is extended or adjusted under 35 U.S.C. 154(b) by 680 days.

(21) Appl. No.: 14/261,586

(22) Filed: Apr. 25, 2014

(65) Prior Publication Data
US 2015/0306220 A1 Oct. 29, 2015

(51) Int. Cl.
*B01J 19/08* (2006.01)
*A61K 9/00* (2006.01)
*A61K 38/17* (2006.01)
*A61K 38/18* (2006.01)
*A61K 47/48* (2006.01)

(52) U.S. Cl.
CPC ........... *B01J 19/087* (2013.01); *A61K 9/0009* (2013.01); *A61K 38/1841* (2013.01); *A61K 47/48861* (2013.01)

(58) Field of Classification Search
CPC .. B01J 19/087; A61K 9/0009; A61K 38/1841; A61K 47/48861
USPC ............... 530/399, 402; 204/155–158.21
See application file for complete search history.

(56) References Cited

U.S. PATENT DOCUMENTS

| | | | |
|---|---|---|---|
| 5,195,940 A | 3/1993 | Baylink | |
| 6,309,633 B1 * | 10/2001 | Ekwuribe | A61K 47/48215 424/193.1 |
| 7,067,129 B2 * | 6/2006 | Blumberg | A61K 38/28 514/7.6 |
| 8,722,855 B2 * | 5/2014 | Ghayur | C07K 16/22 530/388.24 |
| 8,728,463 B2 | 5/2014 | Atala et al. | |
| 2003/0031681 A1 * | 2/2003 | McCart | C12N 15/86 424/186.1 |
| 2003/0092145 A1 * | 5/2003 | Jira | A61K 39/015 424/464 |
| 2005/0095197 A1 * | 5/2005 | Tuszynski | A61K 47/48061 424/1.11 |
| 2012/0121517 A1 * | 5/2012 | Song | A61K 9/0009 424/9.34 |
| 2012/0171744 A1 | 7/2012 | Souza | |
| 2012/0202239 A1 | 8/2012 | Kruglick | |
| 2012/0269721 A1 * | 10/2012 | Weng | A61K 47/488 424/1.11 |
| 2013/0266587 A1 * | 10/2013 | Pitzalis | C07K 16/28 424/172.1 |
| 2014/0274894 A1 * | 9/2014 | Leach | C07K 14/435 514/7.6 |

FOREIGN PATENT DOCUMENTS

| | | |
|---|---|---|
| CA | 2065860 | 3/1991 |
| WO | 2006067080 | 6/2006 |

OTHER PUBLICATIONS

Buscemi et al, "The Single-Molecule Mechanics of the Latent TGF-β1 Complex," Current Biology 21, pp. 2046-2054, Dec. 20, 2011.*
Jasimuddin Ahamed et al. "In vitro and in vivo evidence for shear-induced activation of latent transforming growth factor-β1". Blood. Nov. 2008. vol. 112.

* cited by examiner

*Primary Examiner* — Ibrahime A Abraham
*Assistant Examiner* — Colleen M Raphael
(74) *Attorney, Agent, or Firm* — Thomas Horstemeyer, LLP

(57) ABSTRACT

TGF-β growth factor and its latent complex are conjugated to magnetic micro- or nanoparticles and to magnetic micro- or nanodiscs. By exposing the resulting conjugates to magnetic fields, the TGF-β growth factor can be released from its latent complex in vivo, potentially making it useful in tissue engineering and regenerative medicine. And by exposing a conjugate of TGF-β growth factor and a magnetic particle to a sufficiently strong, radiofrequency magnetic field, the TGF-β growth factor can be denatured and thereby deactivated, potentially making it possible to avoid triggering tumorigenesis, atherosclerosis, fibrotic disease, and cancer.

9 Claims, No Drawings

CONTROLLING THE ACTIVITY OF GROWTH FACTORS, PARTICULARLY TGF-β, IN VIVO

BACKGROUND OF THE INVENTION

The invention relates to cytokines, including growth factors, and more particularly relates to transforming growth factor beta ("TGF-β"). In its most immediate sense, the invention relates to controlling the activity of the TGF-β family of growth factors.

TGF-β has been recognized as having potential for tissue engineering and regenerative medicine. However, TGF-β also has the potential of triggering tumorigenesis, atherosclerosis, fibrotic disease, and cancer. It would therefore be advantageous to provide mechanisms for controlling the activity of TGF-β in vivo.

SUMMARY OF THE INVENTION

The invention proceeds from the realization that conjugating TGF-β and its latent complex to magnetic particles can make it possible to target TGF-13 to specific volumes in a living subject and activate it (via magnetically triggered release from the latent complex) or to denature or change the conformation of TGF-β to deactivate it. More specifically, by conjugating TGF-β and its latent complex to magnetic particles (magnetic micro- or nanoparticles or magnetic micro- or nanodiscs) and then exposing the resulting conjugates to a magnetic field, the TGF-β can be released from its latent complex. Thus, a localized magnetic field can be created in vivo in volumes where the TGF-β is to be activated. When the conjugated TGF-β needs to be inactivated, this can be accomplished by subjecting the conjugate to another magnetic field, which heats the conjugates up, denatures them or induces an irreversible change in conformation, and thereby deactivates them.

DETAILED DESCRIPTION OF PREFERRED EMBODIMENTS

Experiments have shown that surface-functionalized magnetic nanoparticles can be conjugated to TGF-β and to its latent complex. More specifically, experiments have shown that iron oxide magnetic nanoparticles on the order of 50 nm hydrodynamic diameter coated with polyethylene glycol can be conjugated to TGF-β and to its latent complex. It is alternatively possible that such conjugation can also be accomplished using magnetic nanodiscs or magnetic microdiscs of approximately 1 μm diameter and approximately 100 nm thickness. It is also alternatively possible to accomplish such conjugation using magnetic nanoparticles that are coated with gold or dextran, or using permalloy discs in which the top and bottom surfaces are coated with gold while the peripheral edge is uncoated, facilitating conjugation via nickel-NTA linkers.

Experiments have shown that it is possible to release TGF-β from its latent complex by applying a magnetic field to thus-conjugated latent TGF-β complex. These experiments were carried out using radiofrequency fields between approximately 100 kHz and 1 MHz, such as from 110 kHz to 987 kHz at a field strength of 25 mT and from 150 to 400 kHz at a field strength of 41 mT. The mechanism of release in this case may be due to heating of the magnetic iron oxide as it is coupled to the radiofrequency field (though the temperature rise is lower than that required to denature TGF-β. However, TGF-β release may be accomplished otherwise; experiments suggest that low frequency AC magnetic fields from 1 Hz to 100 Hz may also release TGF-β from its latent complex when conjugated to spin vortex discs that oscillate in the AC field. In this case, the release mechanism may be via shear stress on the latent complex during oscillation of the disc in the AC field.

The above experiments indicate that it may be possible to release TGF-β in vivo into a specific volume of interest by introducing into that volume the above-identified conjugates and then superimposing a high-gradient, static magnetic field onto that volume.

If TGF-β is to be deactivated, this can be accomplished by heating, because heating denatures TGF-β or induces irreversible changes in conformation, and therefore deactivates it. For this reason, deactivation of TGF-β can be accomplished by exposing TGF-β conjugates to a sufficiently strong radiofrequency magnetic field. Suitable magnetic nanoparticles for this are iron oxide nanoparticles in the range of 5 nm to 20 nm, coated or complexed with polyethylene glycol, dextran, and/or gold or other biocompatible polymers that can be functionalized.

Although existing experiments have been carried out with TGF-β and latent TGF-β complex, the experimental results would likely be to other growth factors, or cytokines, or another latent growth factor or cytokine complexes.

Although a preferred embodiment has been described above, the invention is defined only by the following claims:

The invention claimed is:
1. A method of releasing active TGF-β from a latent TGF-β complex in which it is sequestered, comprising:
   a. conjugating the latent TGF-β complex to a magnetic nanoparticle; and
   b. exposing the resulting conjugate to a radiofrequency magnetic field between approximately 100 kHz and 1 MHz, wherein the magnetic field heats the magnetic nanoparticle sufficient to release active TGF-β from the latent TGF-β complex.

2. The method of claim 1, wherein the radiofrequency magnetic field has a frequency from 110 kHz to 987 kHz at a field strength of 25 mT.

3. The method of claim 1, wherein the radiofrequency magnetic field has a frequency from 150 to 400 kHz at a field strength of 41 mT.

4. The method of claim 1, wherein the magnetic nanoparticle comprises iron oxide and wherein conjugating the latent TGF-β complex to a magnetic nanoparticle comprises coating the magnetic nanoparticle with at least one of the following: gold, polyethylene glycol, and dextran, and conjugating the latent TGF-β complex to the coating.

5. A method of releasing active TGF-β from a latent TGF-β complex in which it is sequestered, comprising:
   a. conjugating the latent TGF-β complex to a magnetic particle selected from microdisc or nanodisc; and
   b. exposing the resulting conjugate to a low-frequency AC field having a frequency between approximately 1 Hz to 100 Hz, wherein the low-frequency AC field oscillates the microdisk or nanodisc sufficient to release active TGF-β from the latent TGF-β complex.

6. The method of claim 5, wherein conjugating the latent TGF-β complex to a magnetic nanoparticle comprises coating the magnetic nanodisc or microdisc with at least one of the following: gold, polyethylene glycol, and dextran, and conjugating the latent TGF-β complex to the coating.

7. A method of denaturing TGF-β, comprising:
   a. providing TGF-β conjugated to a magnetic nanoparticle; and b. exposing the conjugate to a radiofrequency magnetic field effective to denature the TGF-β that is conjugated to the magnetic nanoparticle.

8. The method of claim 7, wherein the magnetic nanoparticle comprises iron oxide.

9. The method of claim 7, wherein the magnetic nanoparticle is of iron oxide coated with at least one of the following:
  a. gold;
  b. polyethylene glycol;
  c. dextran; and
  d. a biocompatible polymer,
  wherein the coating conjugates the TGF-β to the magnetic nanoparticle.

\* \* \* \* \*